United States Patent
Quinn et al.

(10) Patent No.: US 10,727,956 B2
(45) Date of Patent: Jul. 28, 2020

(54) WIRELESS SENSORS IN MEDICAL ENVIRONMENTS

(71) Applicant: Hill-Rom Services, Inc., Batesville, IN (US)

(72) Inventors: David E. Quinn, Auburn, NY (US); Kenzi L. Mudge, Skaneateles, NY (US); Stephen Embree, Chapel Hill, NC (US); Douglas Seim, Okeana, OH (US); Collin Davidson, Apex, NC (US); Timothy Receveur, Apex, NC (US); Britten Pipher, Raleigh, NC (US)

(73) Assignee: HILL-ROM SERVICES, INC., Batesville, IN (US)

( * ) Notice: Subject to any disclaimer, the term of this patent is extended or adjusted under 35 U.S.C. 154(b) by 0 days.

(21) Appl. No.: 16/120,679

(22) Filed: Sep. 4, 2018

(65) Prior Publication Data

US 2019/0074912 A1    Mar. 7, 2019

Related U.S. Application Data

(60) Provisional application No. 62/554,717, filed on Sep. 6, 2017.

(51) Int. Cl.
| | |
|---|---|
| *H04B 13/00* | (2006.01) |
| *A61B 5/00* | (2006.01) |
| *A61B 5/0205* | (2006.01) |
| *G08B 21/24* | (2006.01) |
| *G08B 25/10* | (2006.01) |

(Continued)

(52) U.S. Cl.
CPC ........... *H04B 13/005* (2013.01); *A61B 5/002* (2013.01); *A61B 5/0008* (2013.01); *A61B 5/0024* (2013.01); *A61B 5/0028* (2013.01); *A61B 5/02055* (2013.01); *A61B 5/6892* (2013.01); *A61B 5/7228* (2013.01); *G08B 21/245* (2013.01); *G08B 25/10* (2013.01); *A61B 5/024* (2013.01); *A61B 5/08* (2013.01); *A61B 90/53* (2016.02)

(58) Field of Classification Search
CPC ..... H04B 13/005; A61B 5/008; A61B 5/0024; A61B 5/0028
See application file for complete search history.

(56) References Cited

U.S. PATENT DOCUMENTS

| | | | |
|---|---|---|---|
| 7,128,741 B1 * | 10/2006 | Isaacson | A61B 18/1402 606/41 |
| 9,000,914 B2 | 4/2015 | Baker et al. | |

(Continued)

*Primary Examiner* — Md K Talukder
(74) *Attorney, Agent, or Firm* — Merchant & Gould P.C.

(57) ABSTRACT

Monitoring a patient can include a vital sign device including a skin contact and a demodulator circuit in communication with the electrically conductive skin contact, the demodulator circuit including: a physiological waveform data processing module configured to process the waveform data received from the electrically conductive skin contact; and a digitally encoded data processing module configured to detect and decode digitally encoded data modulated at the carrier frequency. Also included can be a signal conductive blanket including an extended touch point. A clinician contacts the extended touch point of the signal conductive blanket and the patient monitoring device to connect the vital sign device and the patient monitoring device.

7 Claims, 13 Drawing Sheets

(51) Int. Cl.
   *A61B 5/08*     (2006.01)
   *A61B 90/53*    (2016.01)
   *A61B 5/024*    (2006.01)

(56) References Cited

U.S. PATENT DOCUMENTS

| | | | |
|---|---|---|---|
| 9,579,023 B2 | 2/2017 | Baker et al. | |
| 2008/0004904 A1* | 1/2008 | Tran | A61B 5/0006 705/2 |
| 2009/0099631 A1* | 4/2009 | Augustine | A61F 7/007 607/104 |
| 2009/0233548 A1* | 9/2009 | Andersson | H04B 13/005 455/41.2 |
| 2011/0066044 A1* | 3/2011 | Moon | A61B 5/02125 600/485 |
| 2011/0224498 A1* | 9/2011 | Banet | A61B 5/00 600/300 |
| 2012/0165645 A1* | 6/2012 | Russell | A61B 5/0024 600/388 |
| 2014/0235965 A1* | 8/2014 | Tran | A61B 5/0006 600/301 |
| 2015/0257647 A1* | 9/2015 | Buck | A61B 5/0028 600/388 |
| 2016/0028492 A1* | 1/2016 | Triantafillou | H04W 12/06 726/3 |
| 2017/0055851 A1* | 3/2017 | Al-Ali | A61B 5/053 |
| 2019/0021659 A1* | 1/2019 | Sajwan | A61B 5/6833 |
| 2019/0074912 A1* | 3/2019 | Quinn | H04B 13/005 |
| 2019/0231262 A1* | 8/2019 | Nasry | A61B 1/24 |

\* cited by examiner

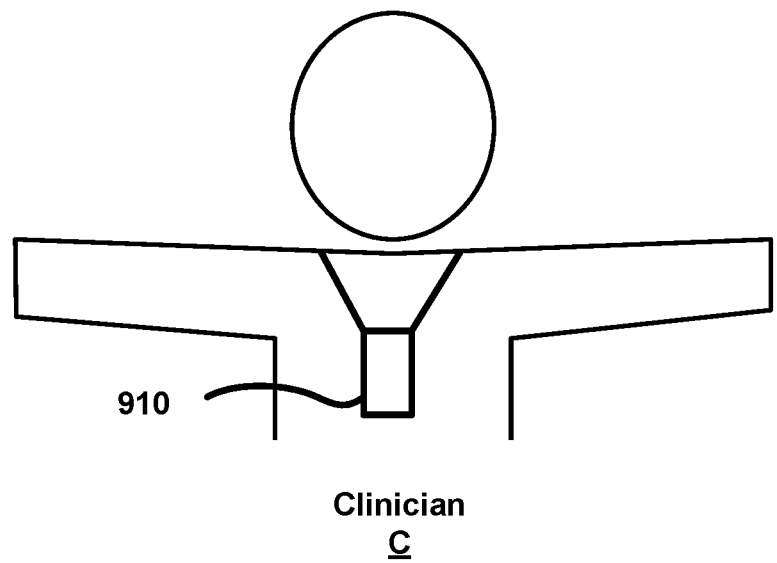
FIG. 10A
FIG. 10B
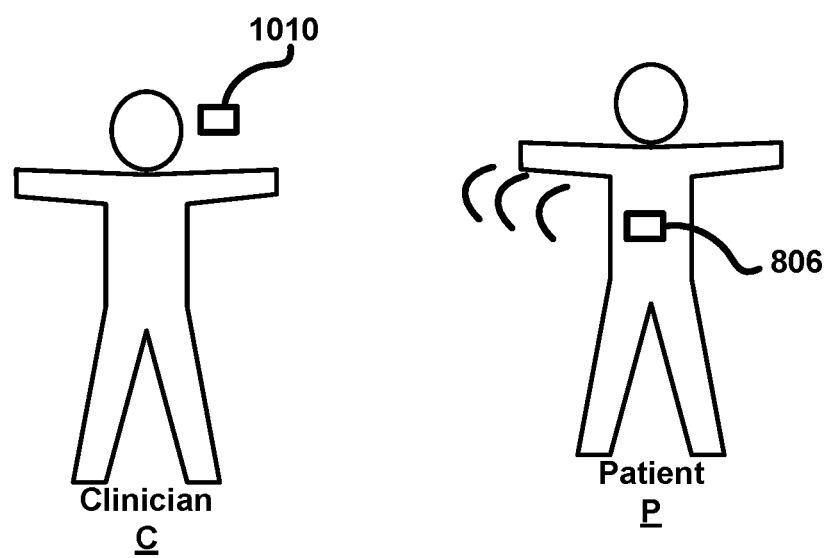

WIRELESS SENSORS IN MEDICAL ENVIRONMENTS

CROSS REFERENCE TO RELATED APPLICATION

The present application claims priority from U.S. Provisional Patent Application No. 62/554,717, filed on Sep. 6, 2017, the disclosure of which is hereby incorporated by reference in its entirety.

BACKGROUND

Personal area networks in a medical setting permit patient sensor data to be efficiently transmitted to a display device. These networks typically use wireless technologies both in sensors attached to the patient and in the display device. Each sensor is typically paired to the display device to enable the transmission of sensor data to the display device. Additionally, patient data is paired with the corresponding patient and/or patient record. In addition to making physiological measurements, other aspects of the care of patients can also be monitored.

SUMMARY

Methods and systems for pairing wireless sensors and display devices are disclosed. In one aspect, a method for connecting a wireless vital sign device and a patient monitoring device is disclosed. The method includes: providing a signal conductive blanket, at least some portion of the signal conductive blanket touching a patient; contacting a portion of the signal conductive blanket; contacting a portion of the patient monitoring device; and confirming, on the patient monitoring device, connection between the vital sign device and the patient monitoring device.

In another aspect, a patient wearable vital sign device is disclosed. The patient wearable vital sign device includes an electrically conductive skin contact configured to obtain waveform data including waveform data modulated at a carrier frequency and a demodulator circuit in communication with the electrically conductive skin contact. The demodulator circuit includes a processor and memory storing instructions that, when executed by the processor, cause the demodulator circuit to provide: a physiological waveform data processing module configured to process the waveform data received from the electrically conductive skin contact and a digitally encoded data processing module configured to detect and decode digitally encoded data modulated at the carrier frequency.

In another aspect, a patient monitoring system is disclosed. The patient monitoring system includes: a vital signs device and a receiver device. The vital signs device includes a physiological sensor module, an alert module, and a non-discernable communication module. The alert module is configured to process data obtained by the physiological sensor module to yield processed physiological data and based on the processed physiological data, determine whether to issue an alert to a clinician. The non-discernable communication path module is capable of emitting the alert in a non-discernable communication path. The receiver device includes a receiving non-discernable communication module capable of receiving data in the non-discernable communication path and a discernable communication alert module capable of emitting a discernable alert to the clinician.

In another aspect, a method for monitoring clinician movement in a patient care room using an asset associated with a clinician is disclosed. The method includes: detecting asset entrance to the patient care room via a door sensor module positioned proximate to a door to the patient care room, detecting asset proximity to a hand wash station in the patient care room via a hand wash station device, detecting asset proximity to a patient bed via a patient bed device, and based on the detecting asset entrance to the patient care room, the detecting asset proximity to the hand wash station, and the detecting asset proximity to the patient bed, determining a clinician compliance with a required workflow.

DESCRIPTION OF THE FIGURES

FIG. 10A shows another example embodiment of a receiver device of the system of FIG. 8.
FIG. 10B shows another example embodiment of a receiver device of the system of FIG. 8.

DETAILED DESCRIPTION

The present disclosure relates to sensors that are used in the context of providing care to a patient. In some examples, the sensors are used to monitor workflows performed when caring for the patient. In these examples, the sensors can be used to minimize the impact of the workflows on the caregiver and/or patient during care.

Figure 1:
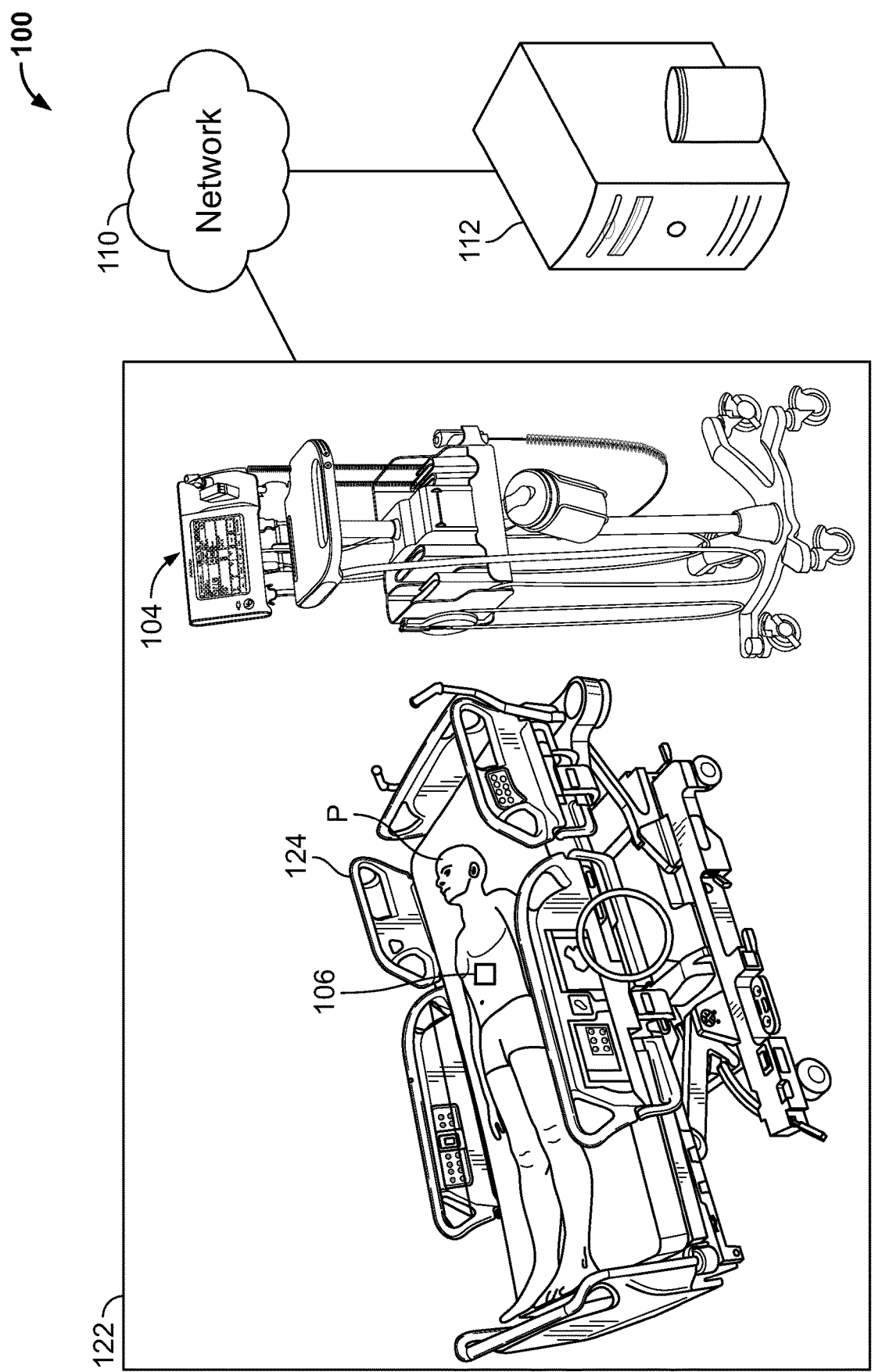
FIG. 1 shows an example system for patient care.

FIG. 1 is a block diagram illustrating an example system 100 for caring for patients. In this example, the system 100 includes patient P located in room 122 of a caregiving facility, such as a hospital or clinic. A wireless sensor 106 is connected to patient P. Patient P is positioned on an example patient support device 124. The room 122 also includes a medical device 104. The medical device 104 is used to assess the patient P using non-invasive procedures. Other embodiments can include more or fewer components.

As noted, the medical device 104 communicates with the network 110. In one example, the medical device 104 and the network 110 are part of a CONNEX™ system from Welch Allyn of Skaneateles Falls, N.Y., although other systems can be used. In such an example, the medical devices communicate through known protocols, such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

Wireless device 106 obtains physiological data of patient P. Wireless device 106 transmits the physiological data to medical device 104 via one or more connection types. For instance, wireless device 106 can be in communication with network 110. As another example, wireless device 106 can communicate data via a connection with the patient's skin. Various embodiments of wireless device 106 are discussed in greater detail below, for instance, with reference to, at least, wireless device 606 and vital signs device 806.

The network 110 is an electronic communication network that facilitates communication between the medical device 104, the mobile device 114, and the server device 112. An electronic communication network is a set of computing devices and links between the computing devices. The computing devices in the network use the links to enable communication among the computing devices in the network. The network 110 can include routers, switches, mobile access points, bridges, hubs, intrusion detection devices, storage devices, standalone server devices, blade server devices, sensors, desktop computers, firewall devices, laptop computers, handheld computers, mobile telephones, medical devices, and other types of computing devices.

In various embodiments, the network 110 includes various types of links. For example, the network 110 can include wired and/or wireless links. Furthermore, in various embodiments, the network 110 is implemented at various scales. For example, the network 110 can be implemented as one or more local area networks (LANs), metropolitan area networks, subnets, wide area networks (such as the Internet), or can be implemented at another scale.

In this example, the medical device 104 and the network 110 are all part of the same network. In other words, the medical device 104 and the network 110 communicate with one another over a LAN behind a digital security layer safeguarding the devices from outside influences on the Internet, such as a firewall.

As noted, the medical device 104 can provide various types of functionality, including measuring or monitoring patient physiological parameters. The medical device 104 can include one or more physiological monitor devices configured to measure and possibly display representations of one or more physiological parameters of a patient. In addition, the medical device 104 can include one or more desktop, laptop, or wall-mounted devices. In some embodiments, the medical device 104 is configured to be used by a clinician to monitor the physiological parameters of multiple patients at one time. Such monitor devices are typically not wall mounted.

In this example, the server device 112 is located "in the cloud." In other words, the server device 112 is located outside of the internal network associated with the medical device 104. Typically, the server device 112 does not communicate directly with the medical device 104, but instead communicates with a central server located within the same network as the medical device 104, such as the CONNEX™ system from Welch Allyn of Skaneateles Falls, N.Y. Intermediary servers in the CONNEX™ system, in turn, communicate with the medical device 104. Other configurations are possible.

The medical device 104 and the server device 112 are computing systems. As used herein, a computing system is a system of one or more computing devices. A computing device is a physical, tangible device that processes data. Example types of computing devices include personal computers, standalone server computers, blade server computers, mainframe computers, handheld computers, smart phones, special purpose computing devices, and other types of devices that process data.

Patient support device 124 provides support for patient P and typically includes a mattress 132, frame 130, and other components. One example of patient support device 124 is the Advanta™ 2 Med Surg Bed manufactured by Hill-Rom of Batesville, Ind.

Figure 2:
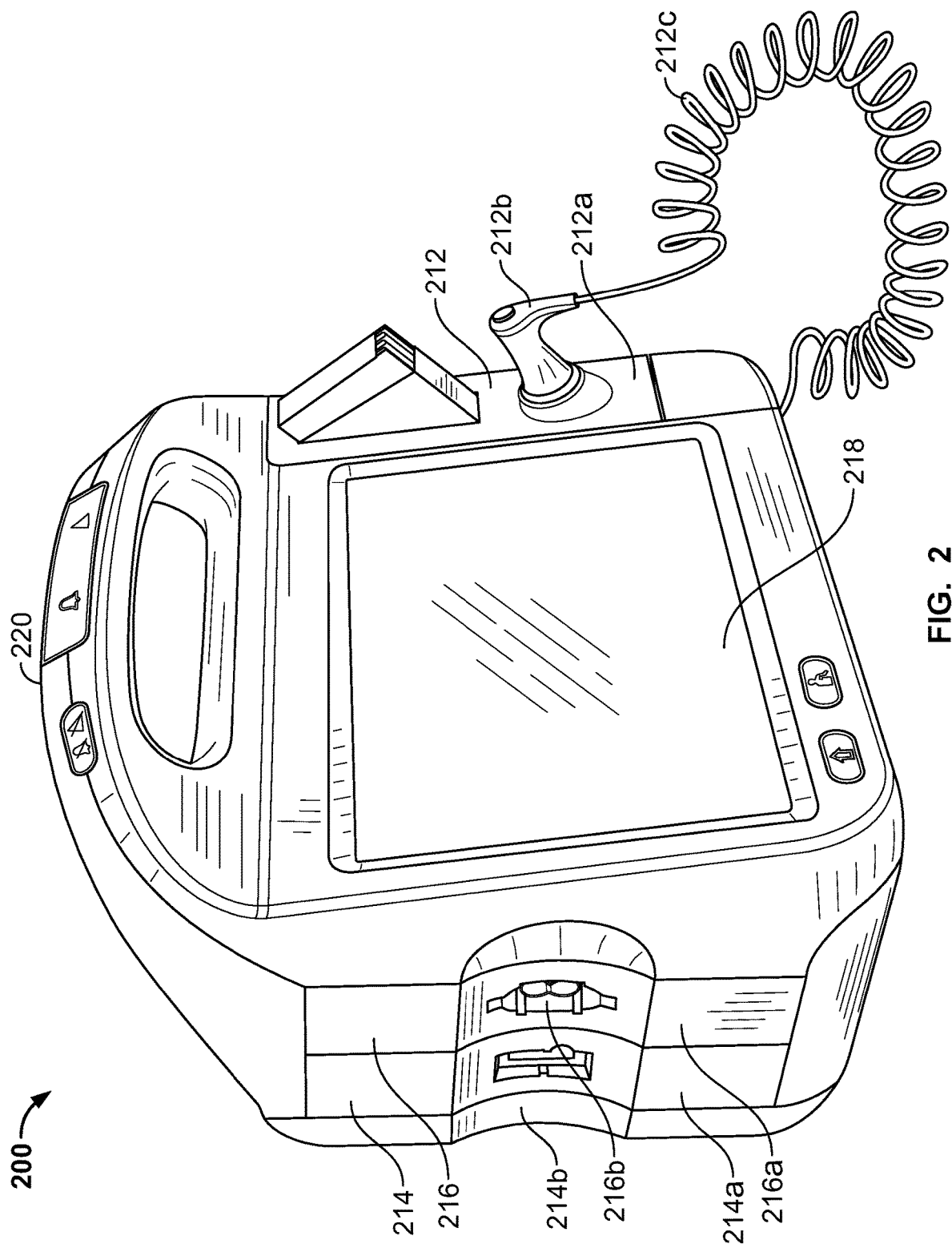
FIG. 2 shows an example medical device of the system of FIG. 1.

FIG. 2 illustrates one example of the medical device 104. A commercially-available example of medical device 104 is the Connex® Spot Monitor available from Welch Allyn® (Skaneateles Falls, N.Y.). The medical device 104 is portable. The medical device 104 includes multiple health care equipment (HCE) modules. Each of the HCE modules is configured to measure one or more physiological parameters of a health-care recipient, also referred to herein as a patient. Other embodiments can include more or fewer components than those shown in FIG. 2, or can include different components that accomplish the same or similar functions.

A temperature measurement module 212 is accessible from the front side of the medical device 104. A SpO2 module 214 and a non-invasive blood pressure (NIBP) module 216 are accessible from a left hand side of the medical device 104. An upper handle portion 220 enables the medical device 104 to be carried by hand.

A front side of the medical device 104 includes a display screen 218 and an outer surface of the temperature measurement module 212. The temperature measurement module 212 is designed to measure the body temperature of a patient. As used in this document, a "module" is a combination of a physical module structure which typically resides within the medical device 104 and optional peripheral components (not shown) that typically attach to and reside outside of the medical device 104.

The temperature measurement module 212 includes a front panel 212a. The front panel 212a has an outer surface that is accessible from the front side of the medical device 104. The front panel 212a provides access to a wall (not shown) storing a removable probe (not shown), also referred to as a temperature probe, that is attached to a probe handle 212b. The probe and its attached probe handle 212b are tethered to the temperature measurement module 212 via an insulated conductor 212c. The probe is designed to make physical contact with a patient in order to sense a body temperature of the patient.

A left hand side of the medical device 104 includes an outer surface of the SpO2 module 214 and an outer surface of the NIBP module 216. The SpO2 module 214 is a HCE module designed to measure oxygen content within the blood of a patient. The NIBP module 216 is a HCE module designed to measure blood pressure of a patient.

As shown, the SpO2 module 214 includes a front panel 214a. The front panel 214a includes an outer surface that is accessible from the left side of the medical device 104. The front panel 214a includes a connector 214b that enables a connection between one or more peripheral SpO2 components (not shown) and a portion of the SpO2 module 214 residing inside the medical device 104. The peripheral SpO2 components reside external to the medical device 104. The peripheral SpO2 components are configured to interoperate with the SpO2 module 214 when connected to the SpO2 module 214 via the connector 214b. In some embodiments, the peripheral SpO2 components include a clip that attaches to an appendage of a patient, such as a finger. The clip is designed to detect and measure a pulse and an oxygen content of blood flowing within the patient.

As shown, the NIBP module 216 includes a front panel 216a having an outer surface that is accessible from the left side of the medical device 104. The front panel 216a includes a connector 216b that enables a connection between one or more peripheral NIBP components (not shown) and a portion of the NIBP module 216 residing inside the medical device 104. The peripheral NIBP components reside external to the medical device 104. The peripheral NIBP components are configured to interoperate with the NIBP module 216 when connected to the NIBP module 216 via the connector 216b. In some embodiments, the peripheral NIBP components include an inflatable cuff that attaches to an appendage of a patient, such as an upper arm of the patient. The inflatable cuff is designed to measure the systolic and diastolic blood pressure of the patient, the mean arterial pressure (MAP) of the patient, and the pulse rate of blood flowing within the patient.

The medical device 104 is able to operate within one or more workflows (or profiles). A workflow is a series of one or more tasks that a user of the medical device 104 performs, typically with a goal of providing patient physiological data into an electronic health record of the patient. When the medical device 104 operates within a workflow, the medical device 104 provides functionality suitable for assisting the user in performing the workflow. When the medical device 104 operates within different workflows, the medical device 104 provides different functionality.

When the medical device 104 is manufactured, the medical device 104 is configured to be able to operate within one or more workflows. After the medical device 104 is manufactured, the medical device 104 can be reconfigured to operate within one or more additional workflows. In this way, a user can adapt the medical device 104 for use in different workflows as needed.

In various embodiments, the medical device 104 operates within various workflows. For example, in some embodiments, the medical device 104 can operate within a monitoring workflow or a non-monitoring workflow. Example types of non-monitoring workflows include, but are not limited to, a spot check workflow, an office workflow, and a triage workflow. A non-limiting example of a monitoring workflow is an intervals workflow.

Figure 3:
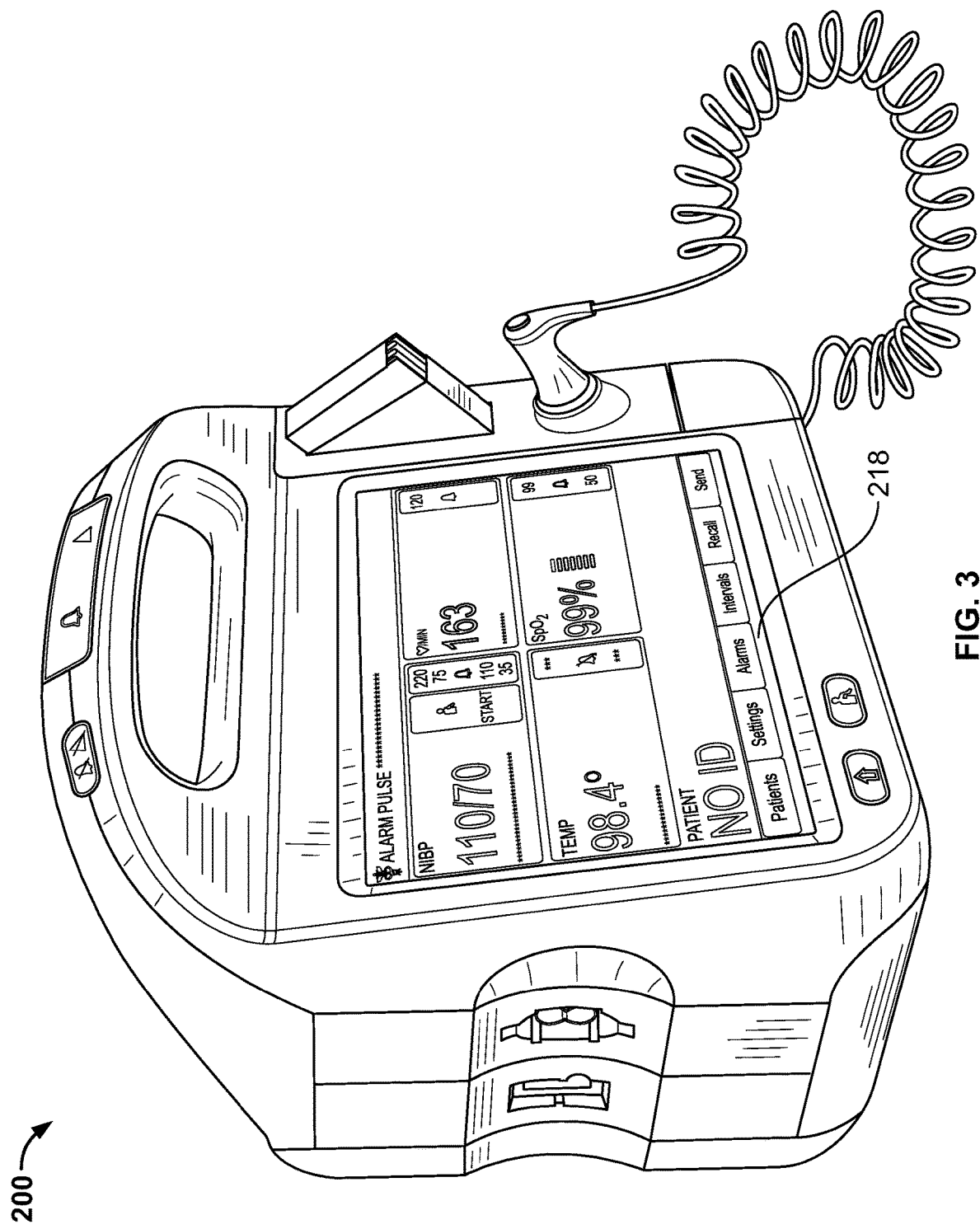
FIG. 3 shows another view of the medical device of FIG. 2.

FIG. 3 illustrates an example user interface displayed on the display screen 218 of FIG. 2. The medical device 104 outputs and displays user interfaces discussed in this document on the display screen 218.

In some examples described herein, the physiological monitor device is a portable device. In other examples, the physiological monitor device is a non-portable device, such as a computing device like a workstation. Many configurations are possible.

The medical device 104 shown in FIGS. 2-3 is only one example of a medical device. All different types of medical devices used to collect patient data can be used.

Figure 4:
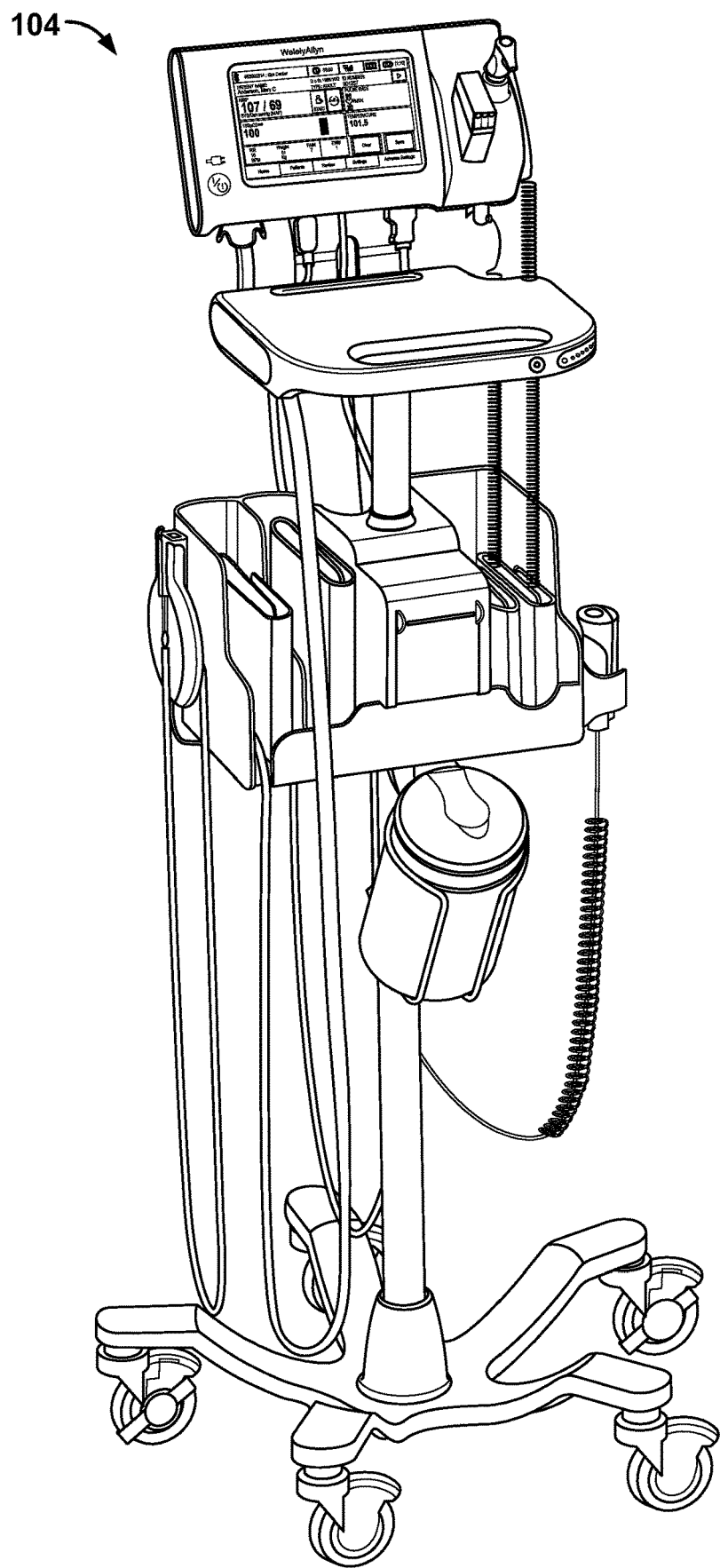
FIG. 4 shows another example medical device of the system of FIG. 1.

For example, another embodiment of the medical device 104 is shown in FIG. 4 on a mobile cart. In some examples, the medical device 104 can be a more compact device that includes a touch screen (e.g., 7 inches) and the ability to execute multiple workflows.

The medical device 104 can be a portable device. In other examples, the medical device 104 can be a stationary device, such as computing devices like workstations. All different types of medical devices used to collect patient data can be used. Many configurations are possible.

Figure 5:
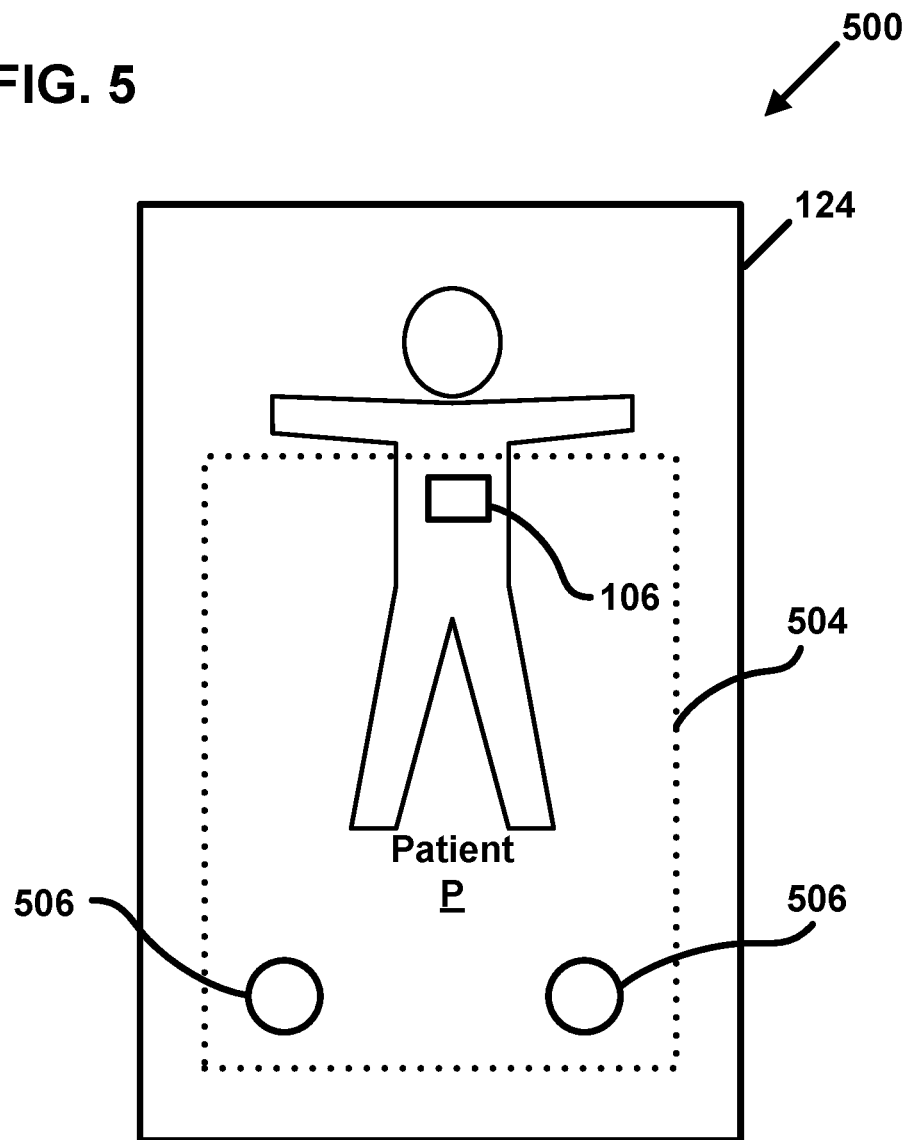
FIG. 5 shows an example patient care system enabled for touch connect pairing.

FIG. 5 illustrates an example system 500 for patient care. Example system 500, which can be implemented with example system 100 discussed above, includes patient support device 124, patient P, wireless sensor 106, and blanket 504. Example system 500 has applications in any of the patient care environments described above. Other embodiments can include more or fewer components.

Example system 500 may be used for touch connect pairing. Touch connect pairing examples are described in greater detail below, but, generally, touch connect pairing is a pairing process between wireless device 106 and a medical device via a person touching both the patient and the medical device. Blanket 504 enables touch connect pairing between wireless device 106 and a medical device without requiring the person, typically a clinician, to touch the patient. Instead, the clinician need only touch blanket 504, or another signal conductive surface coupled to blanket 504, to initiate the touch connect pairing process.

In some instances, the caregiver may not want to touch the patient P, for instance, when the patient P is sleeping and does not need to be woken up for medical care. At the same time, data obtained by wireless device 106 is desired and should have correct patient context. In either scenario, example system 500 enables a clinician to touch blanket 504 and/or patient support device 124 and form a connection with a medical device. This connection is formed without requiring a caregiver to touch patient P. These functionalities are capable because blanket 504 defines at least one path with a series of potentially insulated, often poor conductors that have sufficient capacitive coupling such that a digitally-encoded signal can be demodulated on a receiving end.

Patient support device 124 supports patient P. In some instances, patient support device 124 is mobile, for example having wheels attached thereto, such that patient support device 124 can be moved between various areas, rooms, or floors of the patient care environment. In some instances, a frame defining patient support device 124 includes one or more parts including electrically conductive material. For instance, bed rails, handles, or other parts of patient support device 124 can be constructed in whole or in part of a conductive material.

Blanket 504 is a bedsheet or blanket capable of capacitive coupling with a patient. Blanket 504 typically includes signal conductive material or has conductive threads arranged in a pattern conducive to enhancing capacitive coupling of a digitally-encoded signal. An example digitally-encoded signal is a 100 kHz carrier frequency.

Blanket 504 can be configured to enable capacitive coupling with a clinician at a point away from the patient. In some instances, blanket 504 includes one or more extensions to create a touch point farther away from the patient. An example extension is an extension of the fabric or an electrically conductive wire that connects to blanket 504 via a removable connector, such as a snap button. In some instances, blanket 504 is configured such that it is in contact with, or is attached to the chassis of a frame defining patient support device 124. Thereby, the clinician can capacitively couple to blanket 504 by touching the signal conductive part of the patient support device 124. Blanket 504 can also be shaped such that it fits a medical chair or other furniture that patient P may use in a patient care room.

Blanket 504 is capable of forming a capacitive coupling between wireless device 106 (via the patient's body) and a touch point that is touched by a caregiver. Blanket 504 can include in some instances, specific conductive touch pad areas 506. Alternatively, blanket 504 is conductive enough in all areas and can facility capacitive coupling to the patient's body. In some instances, blanket 504 includes an inner layer of signal conductive blanket with a non-conductive fabric surrounding the inner layer. The addition of a non-conductive fabric surrounding the inner layer may improve patient comfort and the breathability of blanket 504.

Figure 6:
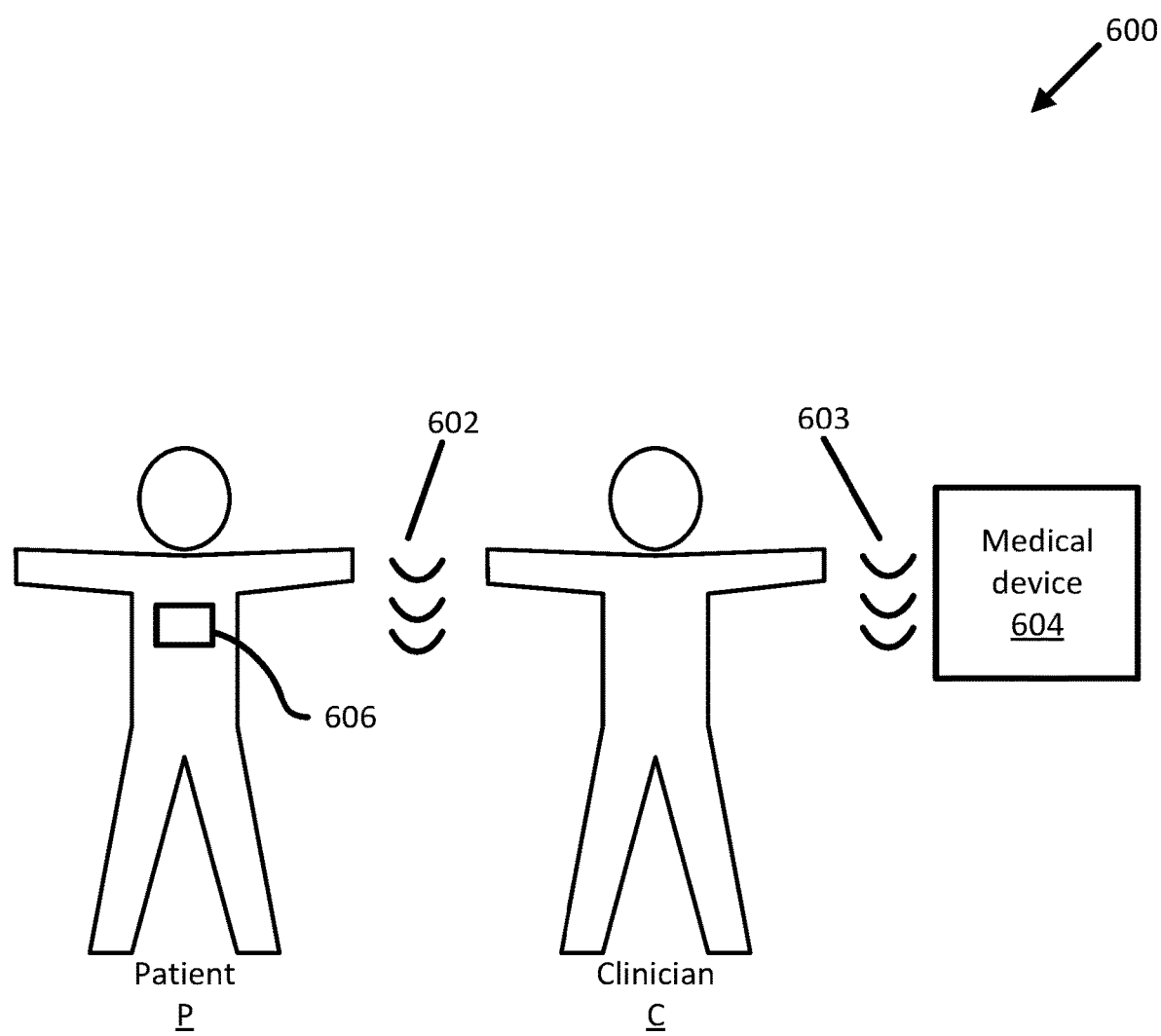
FIG. 6 shows another example patient care system enabled for touch connect pairing.

FIG. 6 is an example patient care system 600 enabled for touch connect pairing. Example patient care system 600 can be implemented with example system 100 discussed above. The example system 600 includes wireless device 606 and medical device 604. Examples of wireless device 606 and medical device 604 are described above with reference to wireless device 106 and medical device 104, respectively. Example components of wireless device 606 are shown and described in greater detail below with reference to FIG. 7. Other embodiments can include more or fewer components.

Wireless device 606 is positioned on patient P. Generally, clinician C completes a path that extends from wireless sensor 606, through the body of patient P, through the body of clinician C, to medical device 604. To do so, clinician C contacts patient P via connection 602 and medical device 604 via connection 603. The path can be contact coupled and/or capacitively coupled.

Typically, wireless device 606 is battery powered. Wireless device 606 is the receiving device in system 600. One or more transmitting units are positioned on medical device 604. In some instances, when wireless device 606 detects a signal from a transmitter (based on connections 602 and 603 and, in some instances, proximity), wireless sensor 606 determines that it is proximal to medical device 604.

Both wireless device 606 and medical device 604 include a Bluetooth radio module. The Bluetooth radio module is capable of communicating via a Bluetooth and/or Bluetooth Low Energy communication protocol. Example systems and methods for body-medium pairing (termed "touch connect pairing" in this disclosure) between wireless device 606 and medical device 604 are shown and described in greater detail in "Personal Area Network Pairing," U.S. Pat. No. 9,000,914, issued Apr. 7, 2015, the entirety of which is hereby incorporated by reference.

Connection 602 enables data communication from wireless device 606 through the body of clinician C. In some instances, connection 602 includes clinician C touching patient P. In some instances, connection 602 includes clinician C touching a conductive intermediary between patient P, such as blanket 504 described above.

Connection 603 enables data communication through the body of clinician C to medical device 604. Typically, connection 603 is formed by clinician C touching a conductive portion of medical device 604.

In a first implementation, the body-medium is used for bi-directional Bluetooth pairing. In a second implementation, the body-medium is used for uni-directional authentication.

Using the body for the medium for Bluetooth out of band (OOB) pairing requires that the wireless sensor 606 paired to medical device 604 provides an electrical or RF connection to the body. When example wireless sensor 606 is attached to the body and is paired with a patient monitor, for example medical device 604, OOB electronics present in wireless sensor 606 modulate a low-current AC signal with OOB Bluetooth pairing information and sends the modulated low-current AC signal to wireless sensor 606 for injection into the body. Typically, the OOB channel is used to provide the address of the Bluetooth transceiver on the medical device 604 and help establish a shared secret for the Bluetooth channel that is not revealed on the Bluetooth channel before it is secured.

The OOB electronics include circuitry that produces the low-current AC signal from a DC power source, typically a battery in the example wireless sensor 606. The modulated low-current AC signal may be continually injected into the body or may be injected into the body periodically. When the low-current AC signal is injected periodically, it may be injected according to a predetermined duty cycle, for example once every second. The signal might only be injected upon an event, such as clinical input, patient motion or other event indicating a state change.

In some instances, a low-current AC signal, typically 100 to 200 microamperes peak to peak, is modulated with OOB BT pairing information. In the modulation process, the carrier is typically an AC signal with a frequency in the 100 kHz range. The pairing data is modulated onto the carrier and becomes the envelope of the modulated AC signal.

Figure 7:
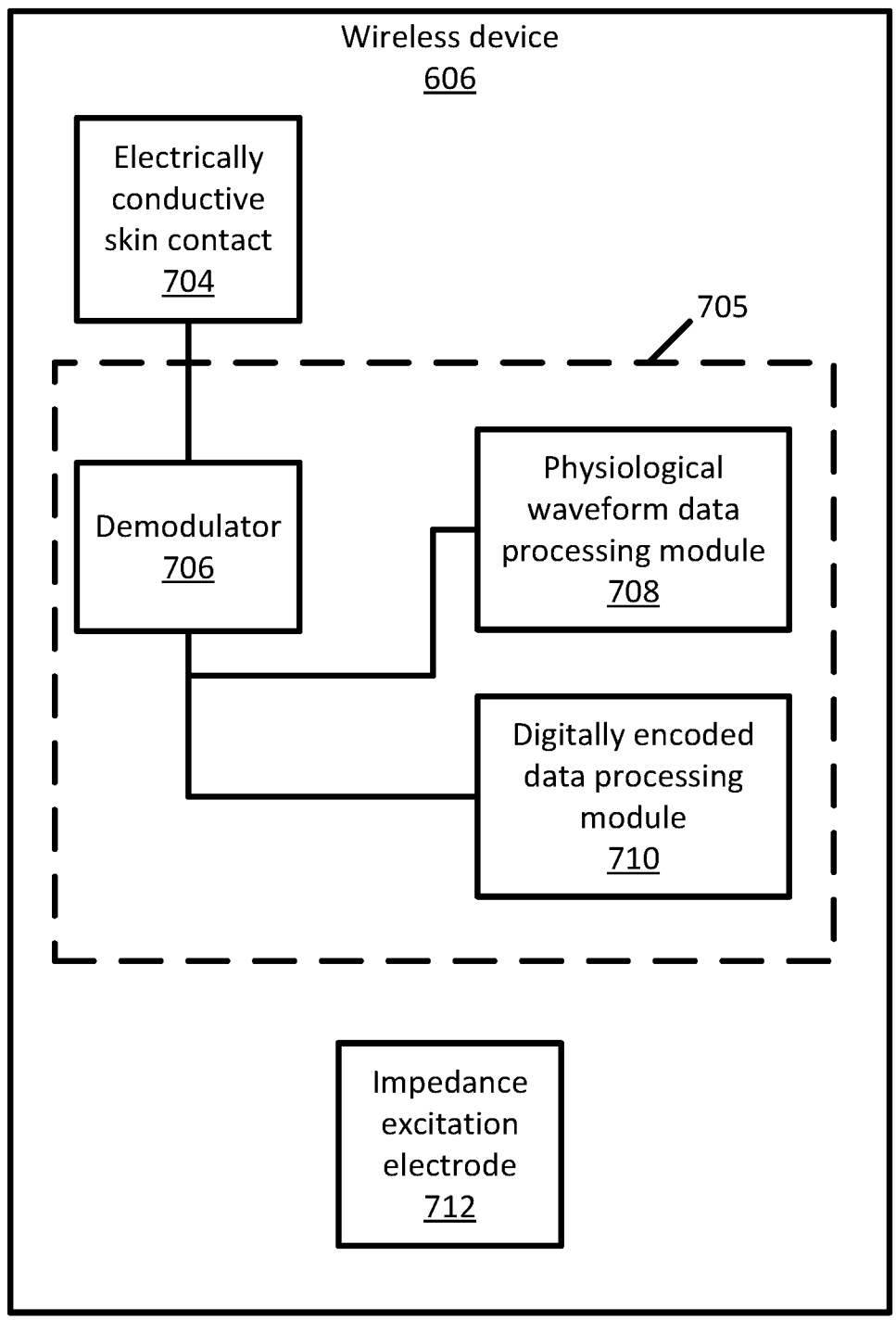
FIG. 7 shows example physical and logical components of the wireless device of FIGS. 1, 6, and/or 7.

FIG. 7 is a schematic block diagram showing example components of wireless device 606. As shown, the example wireless device 606 includes electrically conductive skin contact 704 in communication with dual function impedance receiver 705 and impedance excitation electrode 712. Dual function impedance receiver 705 includes demodulator 706, physiological waveform data processing module 708, and digitally encoded data processing module 710. Typically, physiological waveform data processing module 708 and digitally encoded data processing module 710 are stored in a memory device, such as system memory 1208 described below. Other embodiments can include more or fewer components.

Wireless device 606 is configured to attach to, or be positioned in contact with, skin of a patient. Electrically conductive skin contact 704 acquires one or more types of signal data through its connection to the patient. More specifically, electrically conductive skin contact 704 acquires either physiological data of the patient, such as heart rate, temperature, etc., or encoded body communication data. Data signals acquired by electrically conductive skin contact 704 are communicated to dual function impedance receiver 705, which is tuned to a frequency for physiological impedance measurement, such as 100 kHz.

Broadly, dual function impedance receiver 705 is capable of processing both physiological data communication and encoded body communication data in a single circuit. In that way, dual function impedance receiver 705 eliminates the need for a second receiver circuit, thereby saving the cost of a duplicate receiver circuit and improving the design of wireless device 606 by utilizing an existing connection to utilize one fewer electrode and have a smaller footprint.

Demodulator 706 receives and processes raw impedance signals received from electrically conductive skin contact 704. Demodulator 706 can be implemented as a demodulator circuit. Additionally, demodulator 706 can include a selective filter, such as a 100 kHz selective filter. Dual function impedance receiver 705 can differentiate between incoming body communication data and physiological data. In one instance, differentiation between incoming body communication data versus acquired physiological data occurs by determining an operating state of wireless device 606. That is, if wireless device 606 is not presently outputting a 100 kHz impedance excitation current, then dual function impedance receiver 705 can assume that an incoming signal is from body communication.

Physiological waveform data processing module 708 processes physiological waveforms. Example physiological waveforms include respiration and heart exit volume plethysmograph. Physiological waveform data processing module 708 can communicate processed physiological data to another component of wireless module 606 for transmission to medical device 604.

Digitally encoded data processing module 710 detects and decodes digitally encoded data modulated with the same carrier frequency (e.g., 100 kHz) as that used during physiological data measurement. Digital data received by electrically conductive skin contact 704 can be used during pairing of wireless device 606 and medical device 604. Additionally, digital received by electrically conductive skin contact 704 are capable of bringing wireless device 606 out of a low power or sleep state.

Impedance excitation electrode 712 can induce a carrier frequency into the patient's body during physiological data measurement. Impedance excitation electrode 712 can include one or more electrodes. The one or more electrodes can be configured to induce a carrier frequency of, for instance, 100 kHz. Digitally encoded data processing module 710 can ignore the 100 kHz signal injected for the purpose of vital sign measurement.

Figure 8:
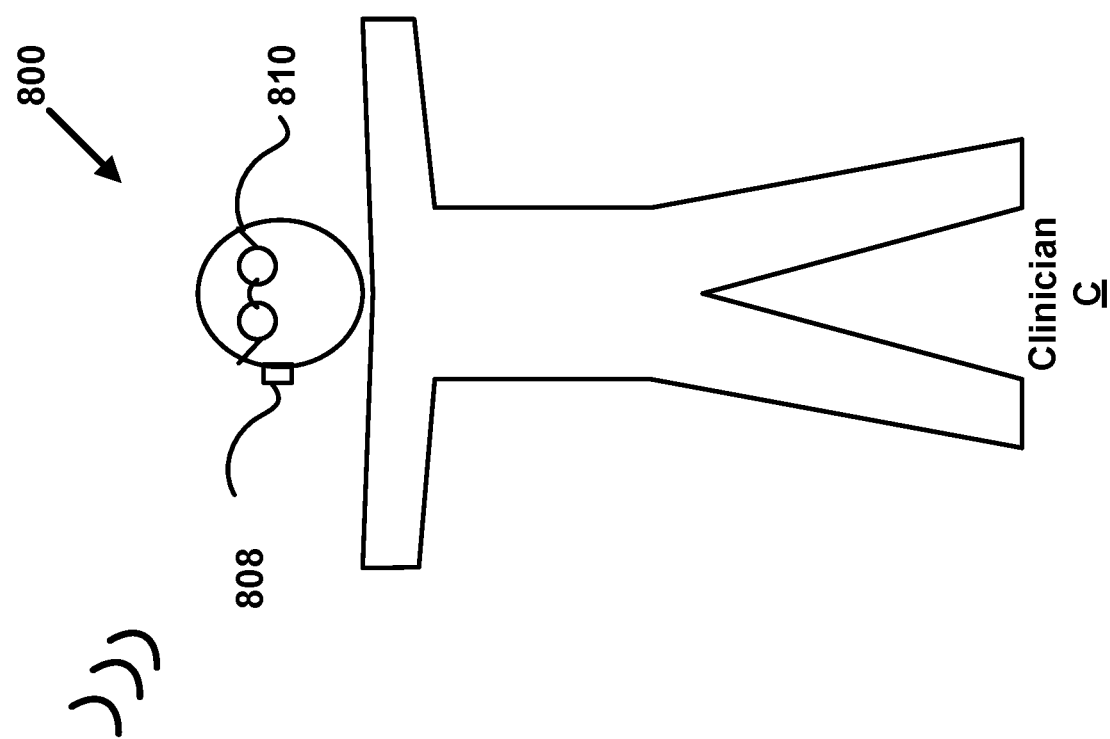
FIG. 8 shows an example system for patient monitoring.
Figure 8:
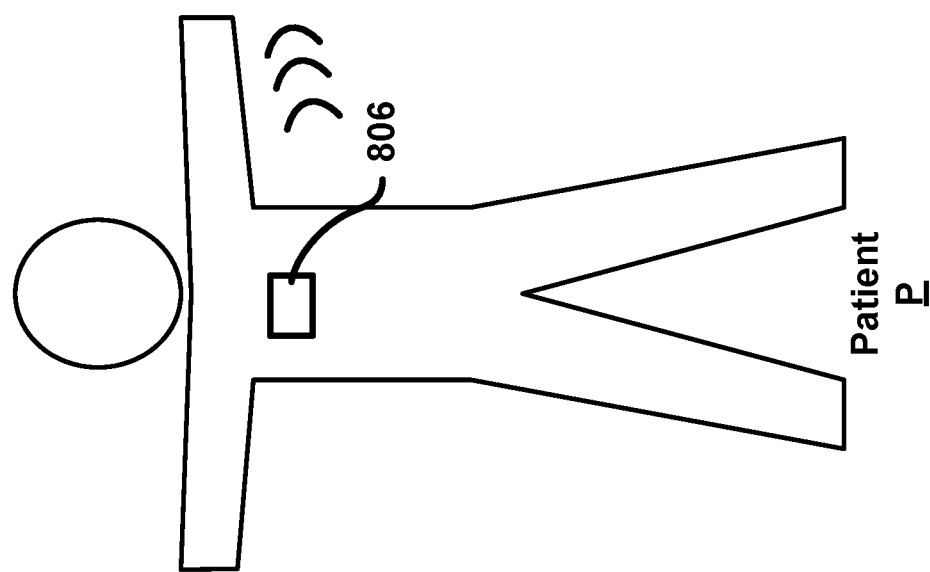

FIG. 8 illustrates an example system 800 for patient monitoring. Example system 800 can be implemented with example system 100 discussed above. The example system includes medical device 804, vital signs device 806, and one or more receiver devices 808, 810. Example configurations of medical device 804 are described above, for instance, with reference to FIG. 1. Example vital signs device 806 is affixed to or placed on patient P. Clinician C has access to, or wears receiver device 808, 810. Other embodiments can include more or fewer components.

Broadly, the example system 800 provides alerts, alarms and/or other notifications to clinician C with minimal disruption to patient P. Indicator lights flashing and audible alarms in the patient care room can keep patient P from sleeping or otherwise disturb patient P. However, clinician C still needs to be able to hear or see alerts about patient P's vital signs. Additionally, patient worn sensors can be covered by blankets or clothing, which can limit or prevent communication of visible and/or audible alerts to clinician C. The example system 800 utilizes alternative devices for delivery of conditions that have minimal impact on the patient P, but clinician C is still notified about the alarms, indicators, alerts, etc., relevant to the patient P's condition.

Figure 11:
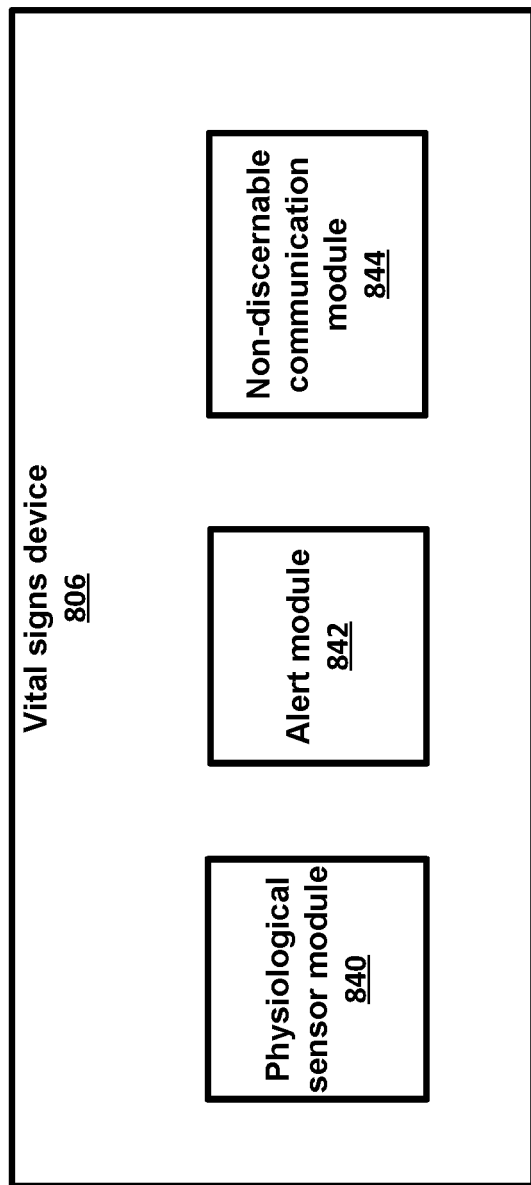
FIG. 11 shows example logical components of the vital signs device of the system of FIG. 8.

Example components of vital signs device 806 are described above with reference to wireless device 106. FIG. 11 shows example logical components of vital signs device 806. Vital signs device 806 includes a physiological sensor module 840, an alert module 842, and a non-discernable communication module 844. The physiological sensor module 840 and alert module 842 process physiological data obtained by wireless device 106 and determine whether to alert or notify clinician C.

If a determination is made to issue an alert or notification, the non-discernable communication module 844 can emit an alert or notification. The alert/notification is transmitted in a non-discernable (to humans) communication medium. Example non-discernable communication paths include infrared light and ultrasonic sound. In some instances, vital signs device 806 communicates the alert to medical device 804 in a non-discernable communication path, and then medical device communicates the alert via to receiver device 808, 810.

Example system 800 can include multiple receiver devices 808, 810. In some instances, clinician C uses only one of receiver devices 808 or 810. In other instances, clinician C utilizes both devices 808 and 810. In one embodiment, receiver device 808 is an ultrasonic converter device.

Figure 9A:
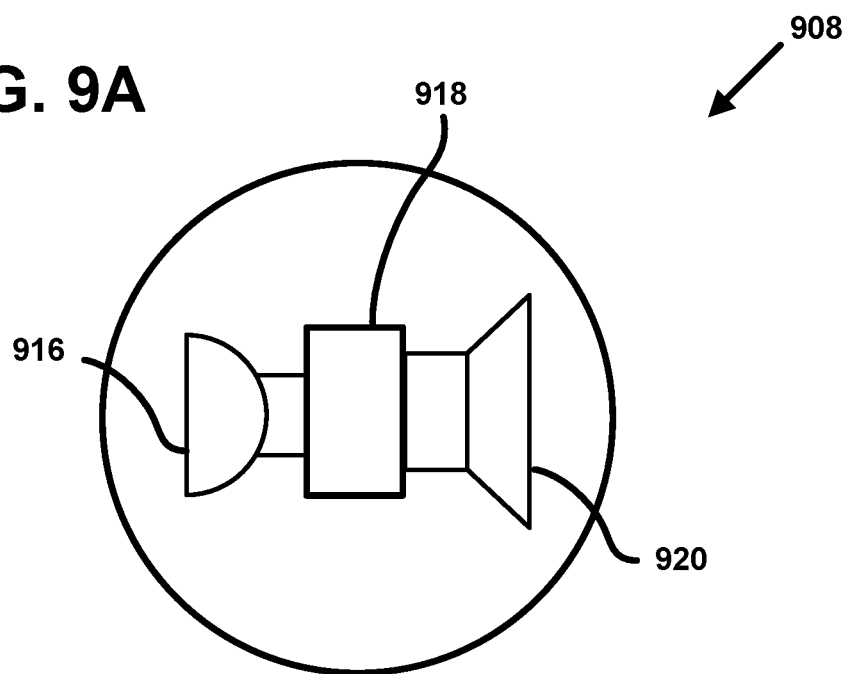
FIG. 9A shows an example embodiment of a receiver device of the system of FIG. 8.

FIG. 9A is a schematic diagram of an example receiver device 908 configured to receive/process ultrasonic sound. Example receiver device 908 is sized and configured to attach to a caregiver, for example, as a button that pins to the caregiver's clothing. Example components of receiver device 908 include an ultrasonic microphone 916, ultrasonic sound conversion module 918, and a speaker 920. Receiver device 908 receives ultrasonic sound via ultrasonic microphone 916, which is configured to detect sound in the ultrasonic frequency. Ultrasonic sound conversion module 918 converts that ultrasonic sound and causes speaker 920 to emit audible sound for clinician C.

Figure 9B:
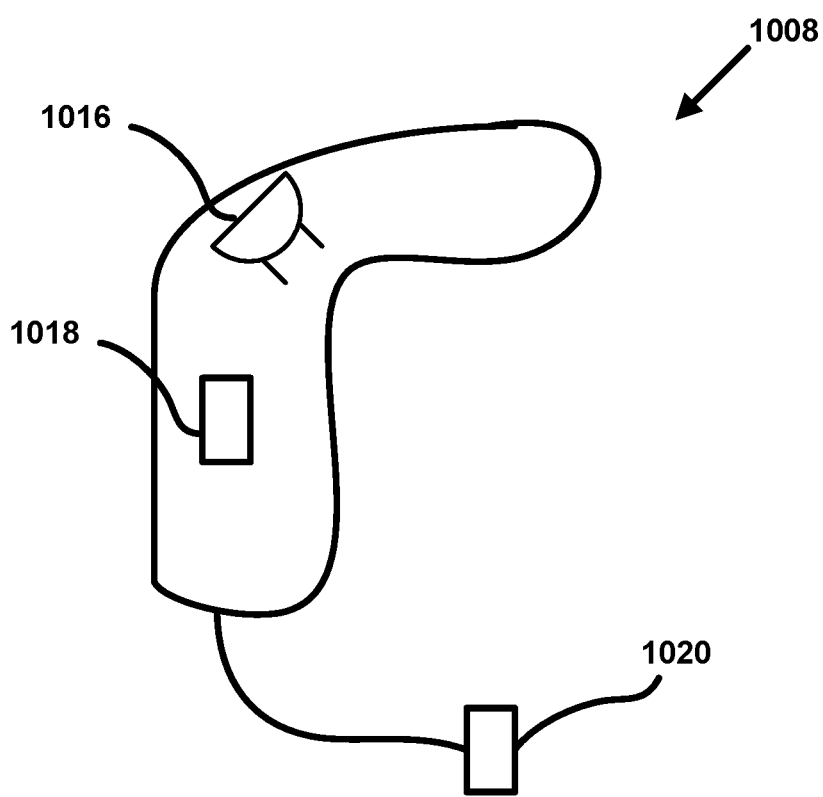
FIG. 9B shows another example embodiment of a receiver device of the system of FIG. 8.

FIG. 9B is a schematic diagram of another example receiver device 1008. Example receiver device 1008 is sized and configured to be worn over an ear of clinician C. Receiver device 1008 includes ultrasonic microphone 1016, ultrasonic sound conversion module 1018, and speaker 1020. Similar to ultrasonic microphone 916, ultrasonic microphone 1016 receives sound in the ultrasonic frequency. Similar to conversion module 918, ultrasonic sound conversion module 1018 converts the ultrasonic sound and causes speaker 1020 to emit audible sound for clinician C. Speaker 1020 can be sized and configured to be worn as an in-ear speaker.

Broadly, receiver device 810 receives infrared emissions from vital signs device 806 and converts those infrared communications to a clinician notification. Clinician notifications can be audible or visible light-based. Example visible light notification includes rendering text or images and illuminating a notification light (e.g., a visible light-emitting diode). In some instances, receiver device 810 shown in FIG. 8 is a wearable device such as infrared light converting glasses. Receiver device 810 receives and processes infrared light using an image sensor array configured to receive infrared light. Then the clinician notification is projected onto the glass len(s) for viewing by the clinician C.

FIGS. 10A and 10B illustrate alternate example receiver devices 910, 1010 capable of use as receiver device 810. Example receiver device 910 includes infrared light processing components as well as visible light notification components similar to those discussed above with reference to receiver device 810. Receiver device 910 can be worn as a lanyard or badge.

Example receiver device 1010 converts infrared light passively, where receiver device 810 is made of material capable of converting infrared light to visible light frequencies. Clinician C can hold example receiver device 1010 on a path between their eyes and wireless device 806. If wireless device 806 is emitting an infrared light signal, receiver device 1010 converts the infrared light to visible light and displays the visible light notification to clinician C.

Figure 12:
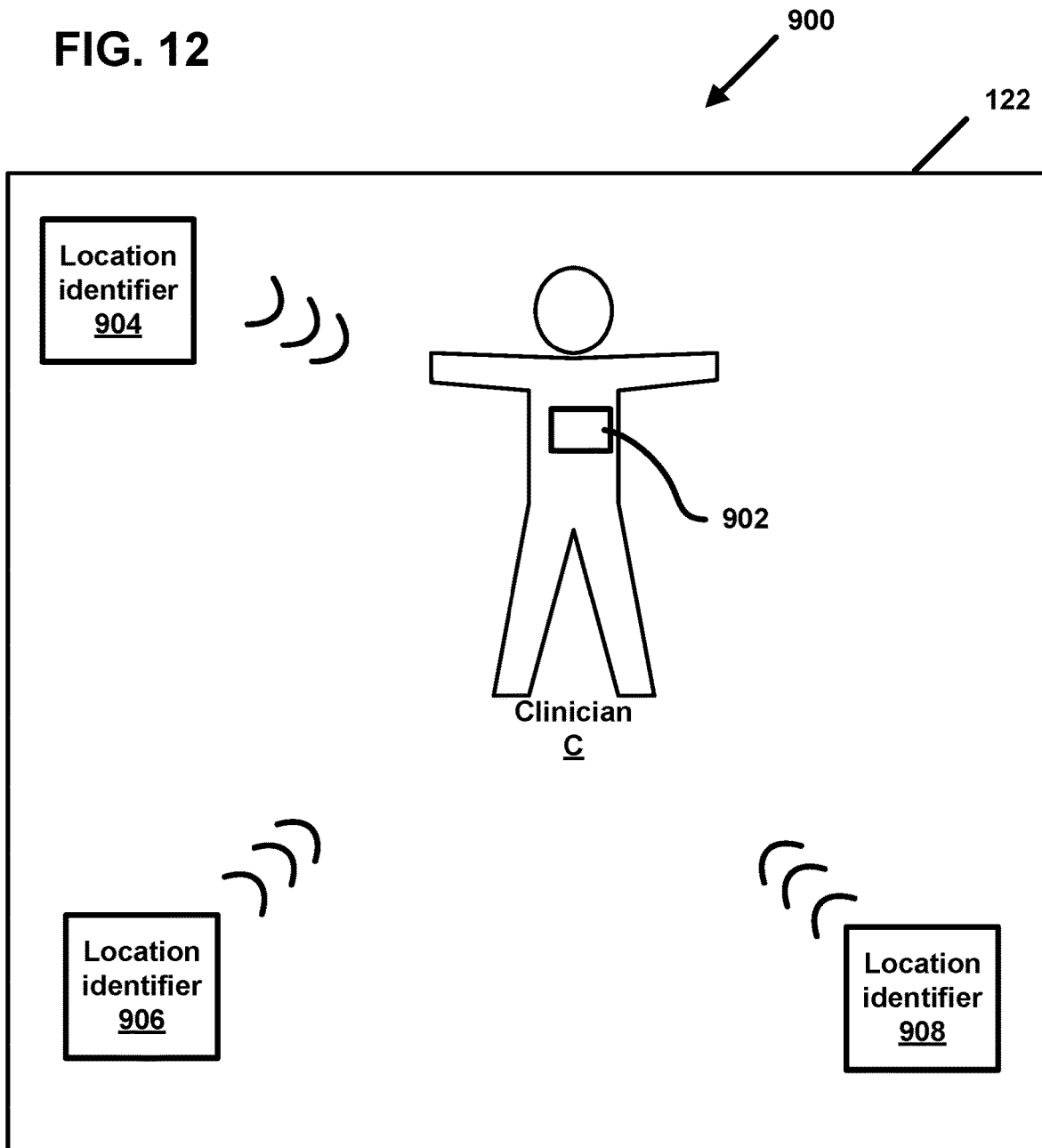
FIG. 12 illustrates an example system for monitoring clinician movement in a patient care room.

FIG. 12 illustrates an example system 900 for monitoring clinician movement in a patient care room 122. Example system 900 can be implemented with example system 100 described above. The example system 900 includes clinician transceiver 902 and one or more location identifier devices 904, 906, 908. Typically, Clinician C wears clinician transceiver 902 or has it on their person. Other embodiments can include more or fewer components.

Broadly, example system 900 can be used to monitor clinician movement in a patient care room. In some instances, data gathered from multiple patient care rooms can be aggregated to provide even more data regarding clinician movement about a patient care facility. Many patient care facilities have predetermined clinician workflow protocols. For instance, clinician workflow protocol can include washing hands immediately upon entry to a patient care room, followed by bedside attendance. Data gathered by system 900 can be used to evaluate and, possibly, educate clinicians working in a particular patient care environment.

One or more location identifier 904, 906, 908 are positioned about room 122. One location identifier, nominally location identifier 904 for purposes of discussion, is typically positioned to determine or detect clinician entrance to room 122. Location identifier 904 is positioned proximate to a door of room 122. In some instances, location identifier 904 is positioned in a door frame of room 122. In some instances, location identifier 904 is positioned in a floor of room 122 proximate to the doorway of room 122. In some instances, location identifier 904 includes sensors positioned both in the floor and in the door frame of room 122.

Location identifiers 906, 908 (and possibly more) are positioned about room 122 proximate to other areas of interest for monitoring. For example, location identifier 906 is positioned at a hand wash station of room 122. As another example, location identifier 908 is positioned at a patient support device 124.

Clinician transceiver 902 communicates wirelessly with location identifier 904, 906, 908. Example clinician transceivers 902 include an employee badge, a fob, a portable computing device such as a smart phone or tablet computer, and the like. Clinician transceiver 902 is configured to communicate a clinician identifier, such as clinician name or employee ID, to location identifier 904, 906, and/or 908 over various wireless protocols. Location identifiers 904, 906, 908 are also configured to communicate wirelessly over one or more wireless protocols. Example wireless protocols include Bluetooth, Bluetooth Low Energy, Near Field Communication (NFC), Welch Allyn Touch Connect, etc.

Figure 13:
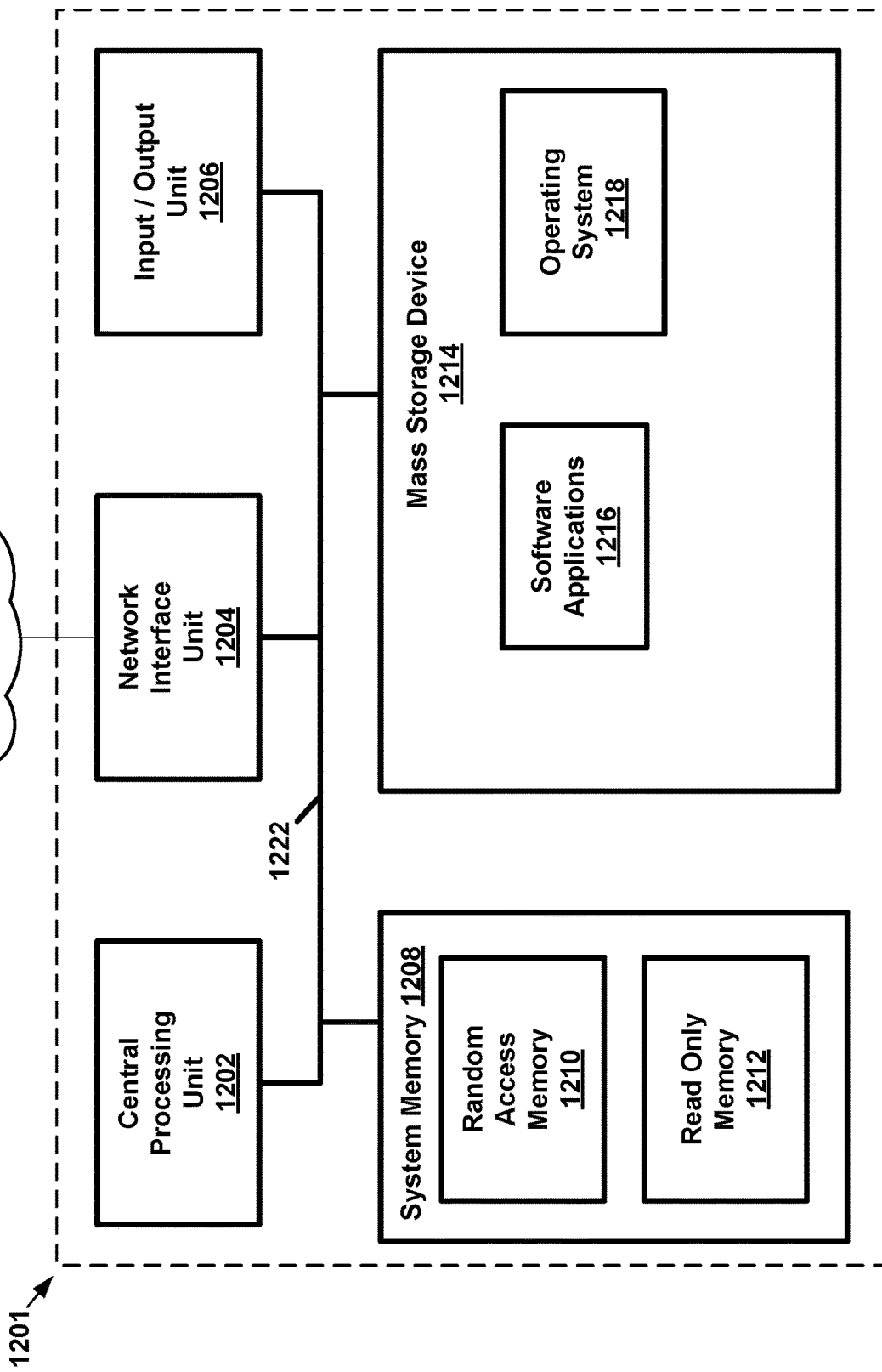
FIG. 13 shows example components of a computing device used in at least some of the devices shown in the Figures.

FIG. 13 illustrates example physical components of a computing device 801, such as the medical device 104 and/or server device 112. As illustrated, the device includes at least one processor or central processing unit ("CPU") 1202, a system memory 1208, and a system bus 1210 that couples the system memory 1208 to the CPU 1202. The system memory 1208 includes a random access memory ("RAM") 1210 and a read-only memory ("ROM") 1212. A basic input/output system containing the basic routines that help to transfer information between elements within the device, such as during startup, is stored in the ROM 1212. The device further includes a mass storage device 1214. The mass storage device 1214 is able to store software instructions and data. The central processing unit 1202 is an example of a processing device.

The mass storage device 1214 is connected to the CPU 1202 through a mass storage controller (not shown) connected to the bus 1222. The mass storage device 1214 and its associated computer-readable data storage media provide non-volatile, non-transitory storage for the device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions. The mass storage device 1214 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the device.

According to various embodiments of the invention, the device may operate in a networked environment using logical connections to remote network devices through the network 110, such as a local network, the Internet, or another type of network. The device connects to the network 110 through a network interface unit 1204 connected to the bus 1222. The network interface unit 1204 may also be utilized to connect to other types of networks and remote computing systems. The device also includes an input/output controller 1206 for receiving and processing input from a number of other devices, including a camera, a keyboard, a mouse, a touch user interface display screen, or another type of input device. Similarly, the input/output controller 1206 may provide output to a touch user interface display screen, a printer, or other type of output device.

As mentioned above, the mass storage device 1214 and the RAM 1210 of the device can store software instructions and data. The software instructions include an operating system 1218 suitable for controlling the operation of the device. The mass storage device 1214 and/or the RAM 1218 also store software instructions 1216, that when executed by the CPU 1202, cause the device to provide the functionality of the device discussed in this document. For example, the mass storage device 1214 and/or the RAM 1210 can store software instructions that, when executed by the CPU 1202, cause the medical and/or mobile device to send or receive physiological measurements.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method for establishing a connection between a wireless vital sign device and a patient monitoring device, the method comprising:
   attaching the wireless vital sign device to a patient;
   providing a signal conductive blanket, at least some portion of the signal conductive blanket touching the patient;
   contacting a portion of the signal conductive blanket with a first clinician body part;
   contacting a portion of the patient monitoring device with a second clinician body part, the patient monitoring device being detached from the patient; and
   confirming, on the patient monitoring device, connection between the vital sign device and the patient monitoring device.

2. The method of claim 1, further comprising contacting an extended touch point on the signal conductive blanket with the first clinician body part.

3. The method of claim 1, wherein the first clinician body part is a first hand of a clinician and the second clinician body part is a second hand of the clinician, the method further comprising:
- allowing the first hand of the clinician to touch an extended touch point on the signal conductive blanket; and
- allowing the second hand of the clinician to touch the portion of the patient monitoring device.

4. The method of claim 1, further comprising forming multiple extended touch points on the signal conductive blanket.

5. The method of claim 4, further comprising forming multiple touch pads on the signal conductive blanket.

6. The method of claim 5, further comprising forming the vital sign device to include an electrically conductive skin contact configured to obtain waveform data including waveform data modulated at a carrier frequency, and a demodulator circuit in communication with the electrically conductive skin contact.

7. The method of claim 1, further comprising contacting an extended touch point on the signal conductive blanket with the first clinician body part, the extended touch point located away from the patient, and contacting an electrically conductive skin contact on the patient monitoring device with the second clinician body part.

\* \* \* \* \*